(12) United States Patent
Northrop et al.

(10) Patent No.: US 8,821,477 B2
(45) Date of Patent: Sep. 2, 2014

(54) ALTERNATIVE MICROMACHINED STRUCTURES

(75) Inventors: Clay W. Northrop, Salt Lake City, UT (US); Ted W. Layman, Park City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1522 days.

(21) Appl. No.: 11/834,508

(22) Filed: Aug. 6, 2007

(65) Prior Publication Data

US 2009/0043372 A1    Feb. 12, 2009

(51) Int. Cl.
*A61M 25/00* (2006.01)

(52) U.S. Cl.
USPC ........ 604/523; 604/264; 604/95.01; 604/524; 604/525; 604/528; 600/585; 600/139

(58) Field of Classification Search
USPC ............... 600/585, 139; 604/95.01, 523–528; 188/367–377; 464/78; 606/127, 128
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

"Mechanical Design and Systems Handbook", H.A. Rothbart, 1964, p. 33-13 (one sheet).

*Primary Examiner* — Victor Nguyen
*Assistant Examiner* — Kevin Everage
(74) *Attorney, Agent, or Firm* — Seager, Tufte & Wickhem, LLC

(57) ABSTRACT

Medical devices and methods for making and using the same. An example medical device may include an elongate core member and a tubular member disposed about a portion of the core member. The tubular member may have a plurality of slots formed therein. The medical devices may be configured to have a preferential bending direction.

12 Claims, 12 Drawing Sheets

(56) References Cited

U.S. PATENT DOCUMENTS

| | | |
|---|---|---|
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A * | 4/1996 | Goode et al. ............... 606/108 |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |

(56) References Cited

U.S. PATENT DOCUMENTS

| | | | |
|---|---|---|---|
| 5,637,089 A | 6/1997 | Abrams et al. | |
| 5,656,011 A | 8/1997 | Uihlein et al. | |
| 5,658,264 A | 8/1997 | Samson et al. | |
| 5,666,968 A | 9/1997 | Imran et al. | |
| 5,666,969 A | 9/1997 | Urick et al. | |
| 5,669,926 A | 9/1997 | Aust et al. | |
| 5,676,659 A | 10/1997 | McGurk | |
| 5,676,697 A | 10/1997 | McDonald | |
| 5,682,894 A | 11/1997 | Orr et al. | |
| 5,690,120 A | 11/1997 | Jacobsen et al. | |
| 5,720,300 A | 2/1998 | Fagan et al. | |
| 5,722,609 A | 3/1998 | Murakami | |
| 5,728,063 A | 3/1998 | Preissman et al. | |
| 5,741,429 A | 4/1998 | Donadio, III et al. | |
| 5,746,701 A | 5/1998 | Noone | |
| 5,769,830 A | 6/1998 | Parker | |
| 5,772,609 A | 6/1998 | Nguyen et al. | |
| 5,782,809 A | 7/1998 | Umeno et al. | |
| 5,788,653 A | 8/1998 | Lorenzo | |
| 5,788,654 A | 8/1998 | Schwager | |
| 5,788,707 A | 8/1998 | Del Toro et al. | |
| 5,792,124 A | 8/1998 | Horrigan et al. | |
| 5,797,856 A | 8/1998 | Frisbie et al. | |
| 5,800,454 A | 9/1998 | Jacobsen et al. | |
| 5,807,075 A | 9/1998 | Jacobsen et al. | |
| 5,807,249 A | 9/1998 | Qin et al. | |
| 5,810,885 A | 9/1998 | Zinger | |
| 5,813,996 A | 9/1998 | St. Germain et al. | |
| 5,827,225 A | 10/1998 | Ma Schwab | |
| 5,827,242 A | 10/1998 | Follmer et al. | |
| 5,833,632 A | 11/1998 | Jacobsen et al. | |
| 5,836,926 A | 11/1998 | Peterson et al. | |
| 5,843,050 A | 12/1998 | Jones et al. | |
| 5,843,244 A | 12/1998 | Pelton et al. | |
| 5,851,203 A | 12/1998 | van Muiden | |
| 5,895,378 A | 4/1999 | Nita | |
| 5,897,537 A | 4/1999 | Berg et al. | |
| 5,902,254 A | 5/1999 | Magram | |
| 5,902,290 A | 5/1999 | Peacock, III et al. | |
| 5,904,657 A | 5/1999 | Unsworth et al. | |
| 5,906,618 A | 5/1999 | Larson, III | |
| 5,911,715 A | 6/1999 | Berg et al. | |
| 5,911,717 A | 6/1999 | Jacobsen et al. | |
| 5,916,177 A | 6/1999 | Schwager | |
| 5,916,178 A | 6/1999 | Noone | |
| 5,916,194 A | 6/1999 | Jacobsen et al. | |
| 5,931,830 A | 8/1999 | Jacobsen et al. | |
| 5,935,108 A | 8/1999 | Katoh et al. | |
| 5,947,940 A | 9/1999 | Beisel | |
| 5,951,539 A | 9/1999 | Nita et al. | |
| 5,971,975 A | 10/1999 | Mills et al. | |
| 5,980,471 A | 11/1999 | Jafari | |
| 6,001,068 A | 12/1999 | Uchino et al. | |
| 6,004,279 A | 12/1999 | Crowley et al. | |
| 6,014,919 A | 1/2000 | Jacobsen et al. | |
| 6,017,319 A | 1/2000 | Jacobsen et al. | |
| 6,022,343 A | 2/2000 | Johnson et al. | |
| 6,022,369 A | 2/2000 | Jacobsen et al. | |
| 6,024,730 A | 2/2000 | Pagan | |
| 6,027,461 A | 2/2000 | Walker et al. | |
| 6,027,863 A | 2/2000 | Donadio, III | |
| 6,042,553 A * | 3/2000 | Solar et al. | 600/585 |
| 6,045,547 A | 4/2000 | Ren et al. | |
| 6,048,339 A | 4/2000 | Zirps et al. | |
| 6,056,702 A | 5/2000 | Lorenzo | |
| 6,063,101 A | 5/2000 | Jacobsen et al. | |
| 6,063,200 A | 5/2000 | Jacobsen et al. | |
| 6,066,361 A | 5/2000 | Jacobsen et al. | |
| 6,106,485 A | 8/2000 | McMahon | |
| 6,106,488 A | 8/2000 | Fleming et al. | |
| 6,139,510 A | 10/2000 | Palermo | |
| 6,165,292 A | 12/2000 | Abrams et al. | |
| 6,171,296 B1 | 1/2001 | Chow | |
| 6,183,410 B1 | 2/2001 | Jacobsen et al. | |
| 6,193,686 B1 | 2/2001 | Estrada et al. | |
| 6,197,014 B1 | 3/2001 | Samson et al. | |
| 6,203,485 B1 | 3/2001 | Urick | |
| RE37,148 E | 4/2001 | Shank | |
| 6,214,042 B1 | 4/2001 | Jacobsen et al. | |
| 6,228,073 B1 | 5/2001 | Noone et al. | |
| 6,248,082 B1 | 6/2001 | Jafari | |
| 6,251,092 B1 | 6/2001 | Qin et al. | |
| 6,254,549 B1 | 7/2001 | Ramzipoor | |
| 6,260,458 B1 | 7/2001 | Jacobsen et al. | |
| 6,273,404 B1 * | 8/2001 | Holman et al. | 264/276 |
| 6,273,876 B1 | 8/2001 | Klima et al. | |
| 6,273,879 B1 | 8/2001 | Keith et al. | |
| 6,290,656 B1 | 9/2001 | Boyle et al. | |
| 6,296,616 B1 | 10/2001 | McMahon | |
| 6,296,631 B2 | 10/2001 | Chow | |
| 6,302,870 B1 | 10/2001 | Jacobsen et al. | |
| 6,325,790 B1 | 12/2001 | Trotta | |
| 6,338,725 B1 | 1/2002 | Hermann et al. | |
| 6,346,091 B1 | 2/2002 | Jacobsen et al. | |
| 6,352,515 B1 | 3/2002 | Anderson et al. | |
| 6,355,005 B1 | 3/2002 | Powell et al. | |
| 6,355,027 B1 | 3/2002 | Le et al. | |
| 6,368,315 B1 | 4/2002 | Gillis et al. | |
| 6,368,316 B1 | 4/2002 | Jansen et al. | |
| 6,375,628 B1 | 4/2002 | Zadno-Azizi et al. | |
| 6,375,774 B1 | 4/2002 | Lunn et al. | |
| 6,379,369 B1 | 4/2002 | Abrams et al. | |
| 6,390,993 B1 | 5/2002 | Cornish et al. | |
| 6,398,758 B1 | 6/2002 | Jacobsen et al. | |
| 6,428,489 B1 | 8/2002 | Jacobsen et al. | |
| 6,428,512 B1 | 8/2002 | Anderson et al. | |
| 6,431,039 B1 | 8/2002 | Jacobsen et al. | |
| 6,440,088 B1 | 8/2002 | Jacobsen | |
| 6,478,778 B1 | 11/2002 | Jacobsen et al. | |
| 6,488,637 B1 | 12/2002 | Eder et al. | |
| 6,491,648 B1 | 12/2002 | Cornish et al. | |
| 6,491,671 B1 | 12/2002 | Larson, III et al. | |
| 6,503,244 B2 | 1/2003 | Hayman | |
| 6,508,803 B1 | 1/2003 | Horikawa et al. | |
| 6,524,301 B1 | 2/2003 | Wilson et al. | |
| 6,530,934 B1 | 3/2003 | Jacobsen et al. | |
| 6,547,779 B2 | 4/2003 | Levine et al. | |
| 6,553,880 B2 | 4/2003 | Jacobsen et al. | |
| 6,556,873 B1 | 4/2003 | Smits | |
| 6,579,246 B2 | 6/2003 | Jacobsen et al. | |
| 6,602,207 B1 | 8/2003 | Mann et al. | |
| 6,602,280 B2 | 8/2003 | Chobotov | |
| 6,610,046 B1 | 8/2003 | Usami et al. | |
| 6,623,448 B2 | 9/2003 | Slater | |
| 6,636,758 B2 | 10/2003 | Sanchez et al. | |
| 6,638,266 B2 | 10/2003 | Wilson et al. | |
| 6,652,508 B2 | 11/2003 | Griffin et al. | |
| 6,682,493 B2 | 1/2004 | Mirigian | |
| 6,689,120 B1 | 2/2004 | Gerdts | |
| 6,702,762 B2 | 3/2004 | Jafari et al. | |
| 6,712,826 B2 | 3/2004 | Lui | |
| 6,730,095 B2 | 5/2004 | Olson, Jr. et al. | |
| 6,749,560 B1 | 6/2004 | Konstorum et al. | |
| 6,766,720 B1 | 7/2004 | Jacobsen et al. | |
| 6,777,644 B2 | 8/2004 | Peacock, III et al. | |
| 6,811,544 B2 | 11/2004 | Schaer | |
| 6,837,898 B2 | 1/2005 | Boyle et al. | |
| 6,866,642 B2 | 3/2005 | Kellerman et al. | |
| 6,887,235 B2 | 5/2005 | O'Connor et al. | |
| 6,918,882 B2 | 7/2005 | Skujins et al. | |
| 6,997,937 B2 | 2/2006 | Jacobsen et al. | |
| 7,001,369 B2 | 2/2006 | Griffin et al. | |
| 7,074,197 B2 | 7/2006 | Reynolds et al. | |
| 7,153,277 B2 | 12/2006 | Skujins et al. | |
| 7,182,735 B2 | 2/2007 | Shireman et al. | |
| 2002/0013540 A1 | 1/2002 | Jacobsen et al. | |
| 2002/0019599 A1 | 2/2002 | Rooney et al. | |
| 2003/0009208 A1 | 1/2003 | Snyder et al. | |
| 2003/0060732 A1 | 3/2003 | Jacobsen et al. | |
| 2003/0069522 A1 | 4/2003 | Jacobsen et al. | |
| 2003/0216668 A1 | 11/2003 | Howland et al. | |
| 2004/0082935 A1 * | 4/2004 | Lee et al. | 604/523 |
| 2004/0116831 A1 | 6/2004 | Vrba | |
| 2004/0142643 A1 | 7/2004 | Miller et al. | |

(56) References Cited

U.S. PATENT DOCUMENTS

| | | | |
|---|---|---|---|
| 2004/0167436 A1 | 8/2004 | Reynolds et al. | |
| 2004/0167437 A1 | 8/2004 | Sharrow et al. | |
| 2004/0167441 A1 | 8/2004 | Reynolds et al. | |
| 2004/0181174 A2* | 9/2004 | Davis et al. | 600/585 |
| 2004/0181176 A1 | 9/2004 | Jafari et al. | |
| 2005/0228481 A1* | 10/2005 | Manasas et al. | 623/1.15 |
| 2006/0121218 A1 | 6/2006 | Obara et al. | |
| 2006/0122537 A1 | 6/2006 | Reynolds et al. | |
| 2006/0189896 A1 | 8/2006 | Davis et al. | |
| 2006/0241564 A1* | 10/2006 | Corcoran et al. | 604/523 |
| 2006/0264904 A1* | 11/2006 | Kerby et al. | 604/523 |
| 2008/0021347 A1 | 1/2008 | Jacobsen et al. | |
| 2008/0021348 A1 | 1/2008 | Jacobsen et al. | |
| 2008/0021400 A1 | 1/2008 | Jacobsen et al. | |
| 2008/0021401 A1 | 1/2008 | Jacobsen et al. | |
| 2008/0021402 A1 | 1/2008 | Jacobsen et al. | |
| 2008/0021403 A1 | 1/2008 | Jacobsen et al. | |
| 2008/0021404 A1 | 1/2008 | Jacobsen et al. | |
| 2008/0021405 A1 | 1/2008 | Jacobsen et al. | |
| 2008/0021406 A1 | 1/2008 | Jacobsen et al. | |
| 2008/0021407 A1 | 1/2008 | Jacobsen et al. | |
| 2008/0021408 A1 | 1/2008 | Jacobsen et al. | |
| 2008/0077119 A1 | 3/2008 | Snyder et al. | |

FOREIGN PATENT DOCUMENTS

| | | |
|---|---|---|
| BR | 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 565 065 | 6/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 0 934 141 | 11/2005 |
| EP | 1709987 | 10/2006 |
| EP | 1457224 | 7/2008 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |
| JP | 7148264 | 6/1995 |
| JP | 7505561 | 6/1995 |
| JP | 7037199 | 7/1995 |
| JP | 7185009 | 7/1995 |
| JP | 7255855 | 10/1995 |
| JP | 7275366 | 10/1995 |
| JP | 751067 | 11/1995 |
| JP | 8-229888 | 9/1996 |
| JP | 8509141 | 10/1996 |
| JP | 8317988 | 12/1996 |
| JP | 9000164 | 4/1997 |
| JP | 9-276413 | 10/1997 |
| JP | 9276413 | 10/1997 |
| JP | 9-294813 A | 11/1997 |
| JP | 9294813 | 11/1997 |
| JP | 10-118193 | 5/1998 |
| JP | 10328191 | 12/1998 |
| JP | 11-267224 A | 10/1999 |
| JP | 2000-197704 A | 7/2000 |
| JP | 2000-510722 A | 8/2000 |
| JP | 2000-511083 A | 8/2000 |
| JP | 2001-500808 A | 1/2001 |
| JP | 3325828 | 7/2002 |
| JP | 2002-529137 A | 9/2002 |
| JP | 2002-542901 A | 12/2002 |
| JP | 2002-543896 A | 12/2002 |
| JP | 2003-517893 A | 6/2003 |
| JP | 3649604 | 2/2005 |
| JP | 2005-534407 | 11/2005 |
| SU | 712908 | 1/1980 |
| SU | 758421 | 8/1980 |
| SU | 1529365 | 12/1989 |
| WO | WO 90/02520 | 3/1990 |
| WO | WO 91/13364 | 9/1991 |
| WO | WO 92/04072 | 3/1992 |
| WO | WO 92/07619 | 5/1992 |
| WO | WO 93/04722 | 3/1993 |
| WO | WO 93/11313 | 6/1993 |
| WO | WO 95/24236 | 9/1995 |
| WO | WO 96/19255 | 6/1996 |
| WO | WO 97/10022 | 3/1997 |
| WO | WO 97/25914 | 7/1997 |
| WO | WO 97/43949 | 11/1997 |
| WO | WO 97/44083 | 11/1997 |
| WO | WO 97/44086 | 11/1997 |
| WO | WO 98/10694 | 3/1998 |
| WO | WO 99/04847 | 2/1999 |
| WO | WO 99/11313 | 3/1999 |
| WO | WO 00/27303 | 5/2000 |
| WO | WO 00/30710 | 6/2000 |
| WO | WO 00/48645 | 8/2000 |
| WO | WO 00/57943 | 10/2000 |
| WO | WO 00/66199 | 11/2000 |
| WO | WO 00/67845 | 11/2000 |
| WO | WO 00/72907 | 12/2000 |
| WO | WO 01/28620 | 4/2001 |
| WO | WO 01/36034 | 5/2001 |
| WO | 0145912 | 6/2001 |
| WO | WO 01/45773 | 6/2001 |
| WO | WO 01/93920 | 12/2001 |
| WO | WO 02/13682 | 2/2002 |
| WO | WO 02/062540 | 8/2002 |
| WO | WO 03/004086 | 1/2003 |
| WO | WO 03/008148 | 1/2003 |

(56) References Cited

FOREIGN PATENT DOCUMENTS

| WO | WO 2004/012804 | 2/2004 |
| WO | 2004047899 | 6/2004 |
| WO | 2004105849 | 12/2004 |
| WO | 2007036815 | 4/2007 |

* cited by examiner

ALTERNATIVE MICROMACHINED STRUCTURES

FIELD OF THE INVENTION

The present invention pertains to medical devices and methods for manufacturing medical devices. More particularly, the present invention pertains to guidewires and catheters that include a slotted tubular member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices or components thereof. An example medical device may include an elongate core member and a tubular member disposed about a portion of the core member. The tubular member may have a plurality of slots formed therein. The medical devices may be configured to have a preferential bending direction.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
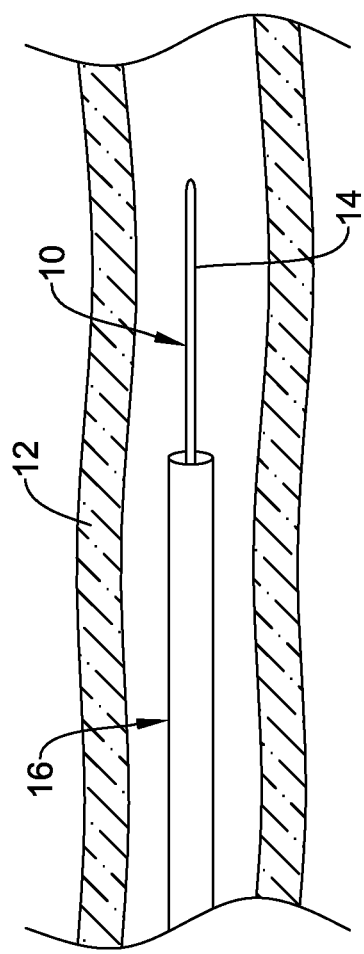
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Figure 2:
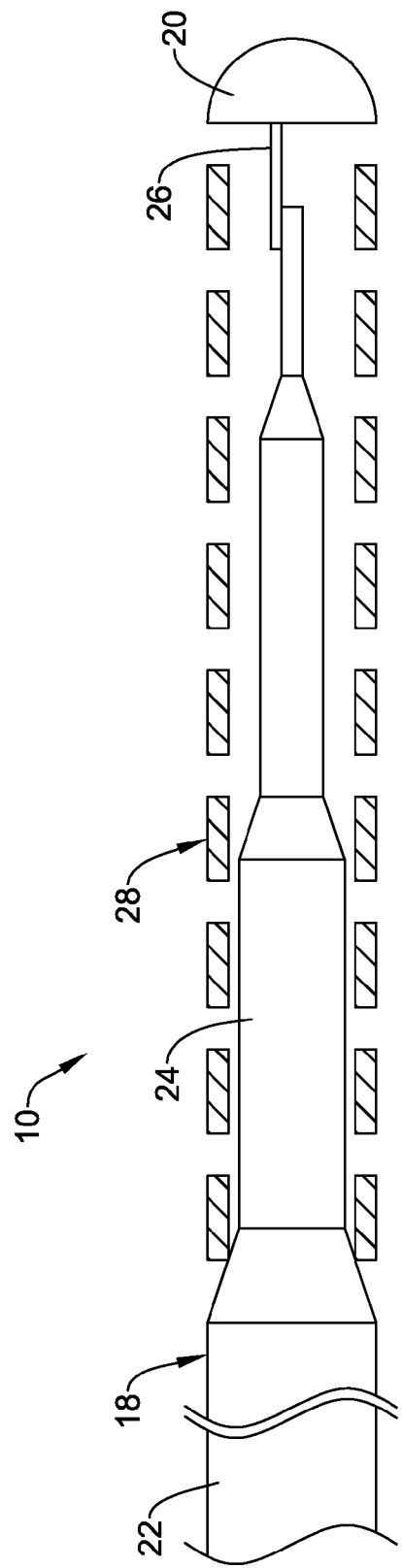
FIG. 2 is a partial cross-sectional side view of an example medical device.

FIG. 2 is a partial cross-sectional view of guidewire 10. Here it can be seen that guidewire 10 may include a core member or core wire 18 and a tubular member 28 disposed over at least a portion of core wire 18. Core wire 18 may include a proximal section 22 and a distal section 24. A connector (not shown) may be disposed between and attach proximal section 22 to distal section 24. Alternatively, core wire 18 may be a unitary member without a connector. A shaping member 26 may be coupled to core wire 18 (for example distal section 24 of core wire 18), tubular member 28, or both. Shaping member 26 may be made from a relatively inelastic material so that a clinician can bend or shape the distal end of guidewire 10 into a shape that may facilitate navigation of guidewire 10 through the anatomy. Some examples of suitable materials for core wire 18, tubular member 28, shaping member 26, etc. can be found below. A tip member 20 may also be coupled to core wire 18, tubular member 28, or both that may define an atraumatic distal tip of guidewire 10. In general, tip member 20 may include solder.

However, other versions of tip member 20 are contemplated including tip members 20 that comprise or form a polymeric tip.

Figure 3:
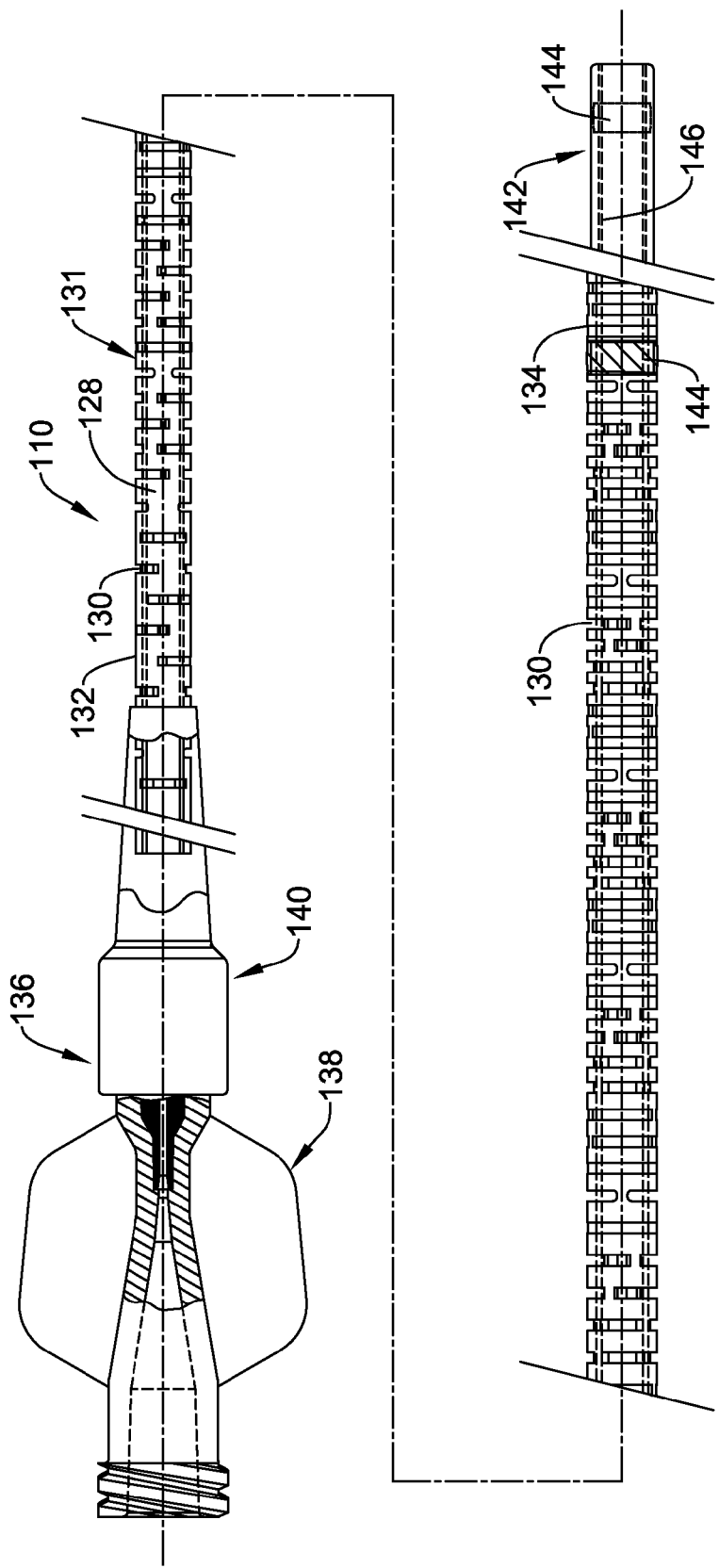
FIG. 3 is a partial cross-sectional side view of another example medical device.

Although medical device 10 is depicted in FIG. 1 as a guidewire, it is not intended to be limited to just being a guidewire. Indeed, medical device 10 may take the form of any suitable guiding, diagnosing, or treating device (including catheters, endoscopic instruments, laparoscopic instruments, etc., and the like) and it may be suitable for use at essentially any location and/or body lumen within a patient. For example, FIG. 3 illustrates another example device 110 in the form of a catheter. Catheter 110 may include a generally elongate shaft 131 having a proximal portion 132 and a distal portion 134. A proximal manifold 136 may be disposed at proximal portion 132. Manifold 136 may include a hub 138 and strain relief 140. A tip member 142 may be disposed at distal portion 134. Tip member 142 may include a radiopaque marker member 144. One or more additional marker members 144 may be disposed along other portions of catheter 110, for example along distal portion 134 of shaft 131. Shaft 131 may include a tubular member 128 that may be similar in form and function to other tubular members disclosed herein including tubular member 28. Tubular member 128 may have a plurality of slots 130 formed therein. A liner 146 may be disposed within tubular member 128. Liner 146 may be similar to the analogous structure disclosed in U.S. Pat. No. 7,001,369 and U.S. Patent Application Publication No. US 2006/0264904, the entire disclosures of which are herein incorporated by reference.

Figure 4:
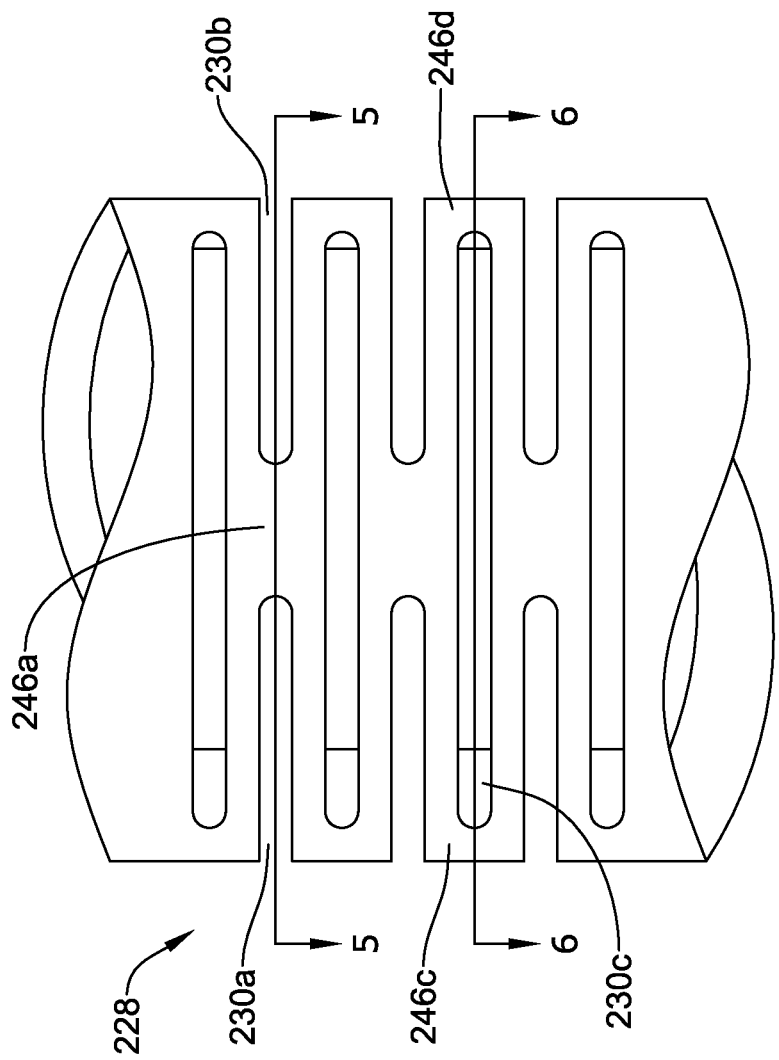
FIG. 4 is a perspective view of a portion of an example tubular member.
Figure 5:
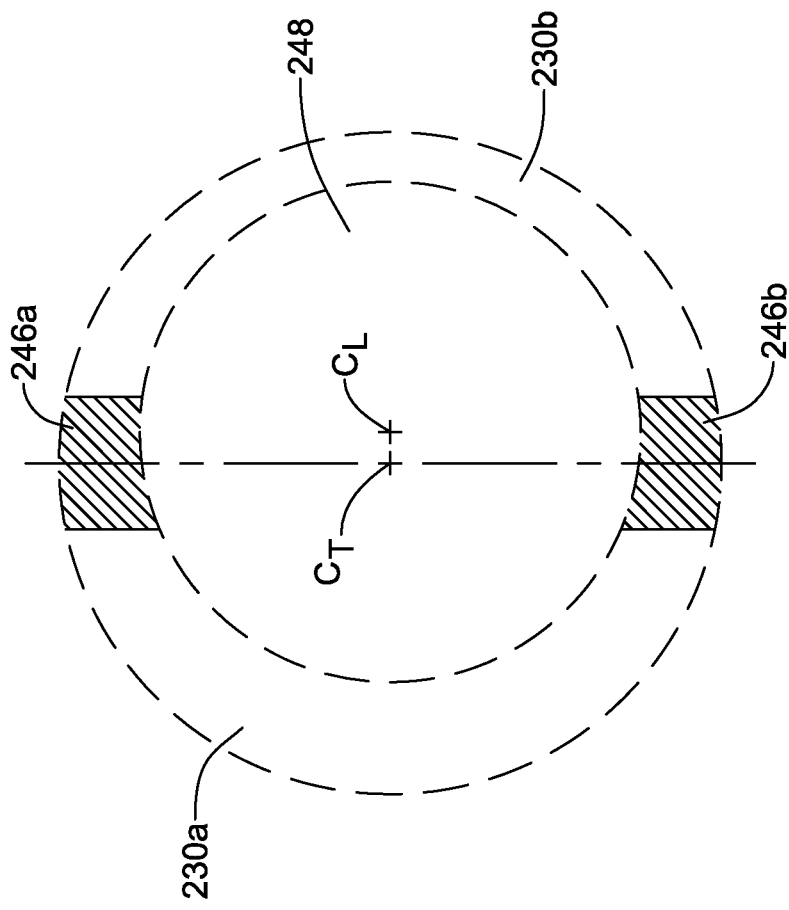
FIG. 5 is a cross-sectional view taken through line 5-5 in FIG. 4.
Figure 6:
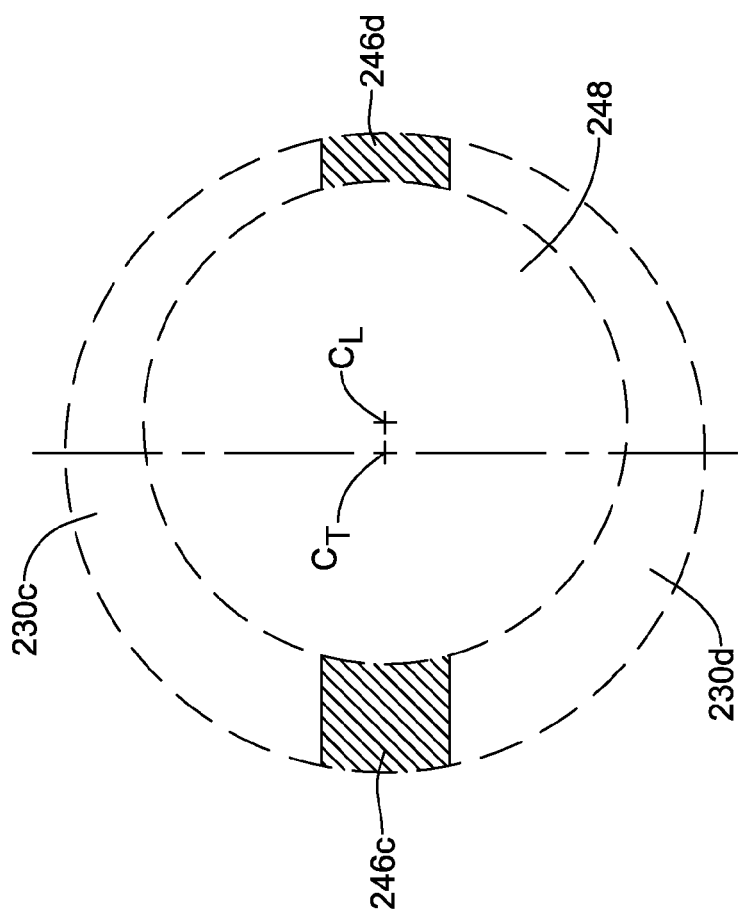
FIG. 6 is a cross-sectional view taken through line 6-6 in FIG. 4.

With the above example devices 10/110 in mind, refer now to FIGS. 4-6, which illustrates an example tubular member 228. It can be appreciated that tubular member 228 may represent the tubular member (e.g., tubular members 28/128) found in either or both of devices 10/110. As such, discussion pertaining to tubular member 228 (or other tubular members disclosed herein) may be applied to tubular member 28 and/or tubular member 128 without departing from the spirit of the invention.

As shown in FIG. 4, tubular member 228 may have a plurality of slots 230a/230b/230c/230d (slot 230d is more clearly seen in FIG. 6) formed therein. Generally, slots 230a/230b/230c/230d are formed by making a pair of cuts into the wall of tubular member 228 that originate from opposite sides of tubular member 228. After making the pair of cuts, the uncut portions of tubular member 228, which may be called "beams", are left behind between the slots. For example, between slots 230a and 230b, a pair of beams 246a and 246b (best seen in FIG. 5) are defined. Likewise, between slots 230c and 230d, another pair of beams 246c and 246d are defined. This pattern may repeat along the length of tubular member 28 or it may vary. Some further discussion regarding slot and/or beam arrangements are described in more detail below.

Turning now to FIG. 5, here it can be seen that tubular member 228 has an eccentric lumen 248. For the purposes of this disclosure, being eccentric is understood to mean that the outer periphery of lumen 248 is eccentrically arranged relative to the outer wall of tubular member 228. Accordingly, the centerline of the lumen, $C_L$, is offset relative to the centerline of tubular member 228, $C_T$. Because of the eccentric nature of lumen 248, one side of tubular member 228 can be seen as having a thicker wall. For example, the portion of tubular member 228 that is removed to define slot 230a can be seen in FIG. 5 as being thicker than the portion removed to define slot 230b. This feature can also be seen in FIG. 6 where beam 246c has a greater thickness than beam 246d. This general eccentric arrangement may hold true along all or a portion of the length of tubular member 228.

The eccentric arrangement of lumen 248 may provide tubular member 228 with a number of desirable features. For example, because the tube wall on one side of tubular member 228 may be thicker than another side opposite the first side, tubular member 228 may have a preferential bending direction. A preferential bending direction may be understood to mean that tubular member 228 bends more easily in one direction than another (i.e., tubular member 228 has a lateral flexibility that requires less force to bend it in the preferential bending direction than any other direction). Generally, tubular member 228 is easiest to bend or curve in the preferential bending direction. Directly opposite the preferential bending direction, tubular member 228 may or may not have a more difficult or "least preferential bending direction" (i.e., tubular member 228 has a lateral flexibility that requires more force to bend it in a direction opposite the preferential bending direction than any other direction). Between the preferential bending direction and the direction opposite the preferential bending direction, tubular member 228 may transition in lateral flexibility between that of the preferential bending direction and that opposite thereof.

Having a preferential bending direction may be desirable for a number of reasons. For example, some interventions may include navigating tubular member 228 (i.e., the appropriate device including tubular member 228) to a target location. The target location may be within vasculature such that tubular member 228 may need to navigate a series of bends or curves in the vasculature. At least some of these bends may be known by the clinician prior to the intervention. Accordingly, the clinician may wish to select a particular device based on it bending characteristics so that the clinician can successfully navigate the device through the anatomy. By selecting a device with a preferential bending direction, the clinician may align the device with the appropriate portion of the anatomy and then use the relative "ease" in bending the device in a particular direction to cause the device to easily and predictably bend around the corresponding part of the anatomy.

In some embodiments, a "tension member" may be disposed adjacent or within tubular member 228 or any of the other tubular members disclosed herein. In embodiments where tubular member 228 is part of guidewire 10, the tension member may be core member 18. In embodiments where tubular member 228 is part of catheter 110, the tension member may be liner 146. Alternatively, the tension member may take the form of another tensioning wire, a pull wire, or the like that can be used to apply tension on tubular member 228 in either of devices 10/110. In still other embodiments, hydraulic pressure can be applied to device 10/110 so as to create the desired level of tension. The application of tension on tubular member 228 may cause tubular member 228 to bend toward its preferential bending direction. Thus, including a tension member may cause device 10/110 to have a curved portion (e.g., a curved tip) that may desirably impact the ability of a clinician to advance device 10/110 through the anatomy.

In at least some embodiments, the tension member may be accessible at the proximal end of device 10/110. Thus, the clinician can apply force to the tension member so as to cause a portion of device 10/110. In some cases, the amount of tension can be selectively changed by the clinician. Changing the tension may cause a curve or bend along the preferential bending direction to increase or decrease. In other embodiments, device 10/110 is available "pre-tensioned" so that device 10/110 has a predetermined bend. The amount of pre-tensioning can vary widely as can, analogous, the variety of curves resulting therefrom.

Figure 7:
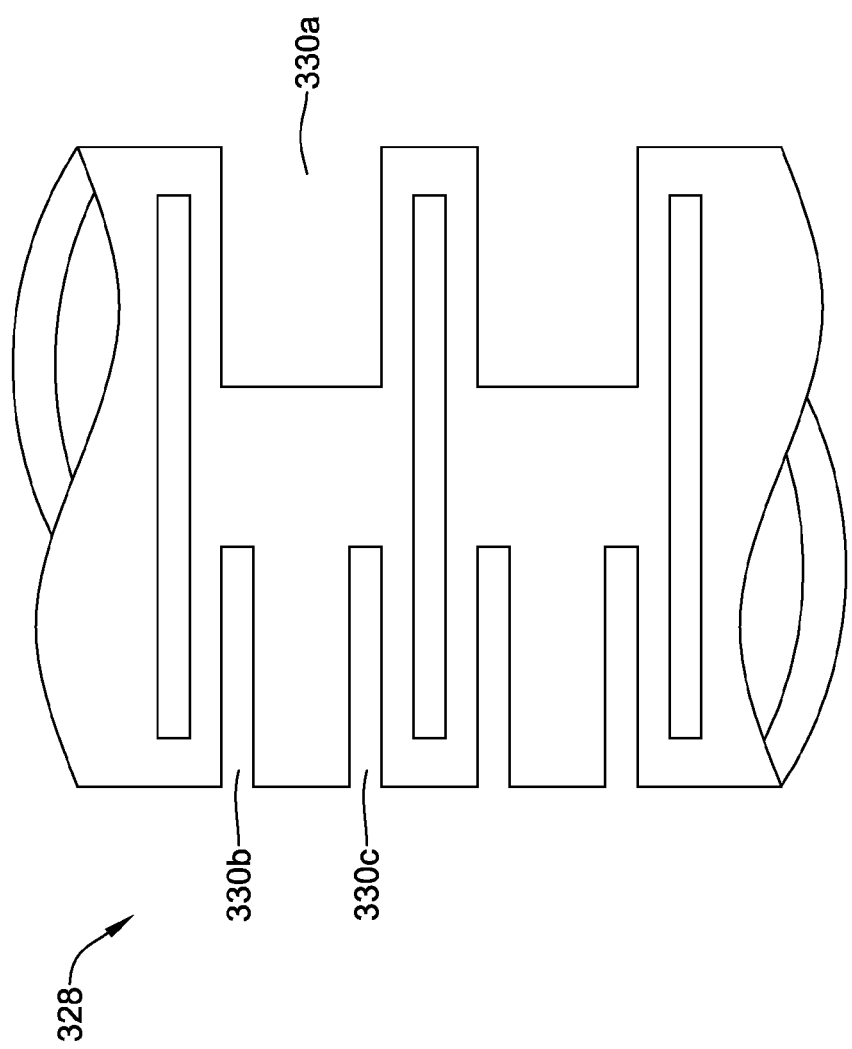
FIG. 7 is a perspective view of a portion of another example tubular member.

A number of additional embodiments of tubular members are contemplated with preferential bending directions. For example, FIG. 7 illustrates another tubular member 328 that has a generally "wide" slot 330a along one side and a plurality of "narrow" slots 330b/330c opposite wide slot 330a. Slots 330a/330b/330c may be formed in any suitable manner including through the use of the methods described below. Wide slot 330a, by virtue of being wider than slots 330b/330c, may be formed through multiple passes of the appropriate cutting device (e.g., saw blade, laser, etc.) to achieve the increased width.

As shown in FIG. 7, two narrow slots 330b/330c are disposed directly opposite wide slot 330a. As such, wide slots 330a may be about twice or more as wide as slots 330b/330c. The exact widths of slots 330a/330b/330c, however, can vary any include any suitable width. In other embodiments, the arrangement of slots 330a/330b/330c may be altered so that more than two narrow slots are disposed opposite wide slot 330a. In these embodiments, the width of wide slots 330a and/or the width of narrow slots 330b/330c can vary to be "wider" or "narrower", as desired. In addition, tubular member 328 may include some wide slots 330a with one, two, three, or more narrow slots opposite it and other wide slots 330a with the same or a different number of slots opposite it (including wide and/or narrow slots). In some embodiments, all the wide slots 330a are disposed along the same side of tubular member 328 and all the narrow slots 330b/330c are disposed on the opposite side. In other embodiments, however, wide slots 330a and/or narrow slots 330b/330c can be distributed on either side of tubular member 328 in any suitable pattern or arrangement.

It can be appreciated that a preferential bending direction may be defined along the side of tubular member 328 where wide slots 330a are positioned. Along the opposite side (e.g., wherein slots 330b/330c are positioned), tubular member 328 may or may not have a more difficult or "least preferential bending direction". The most/least preferential bending directions may be desirable for the same reasons described above as well as for a number of additional reasons.

Figure 8:
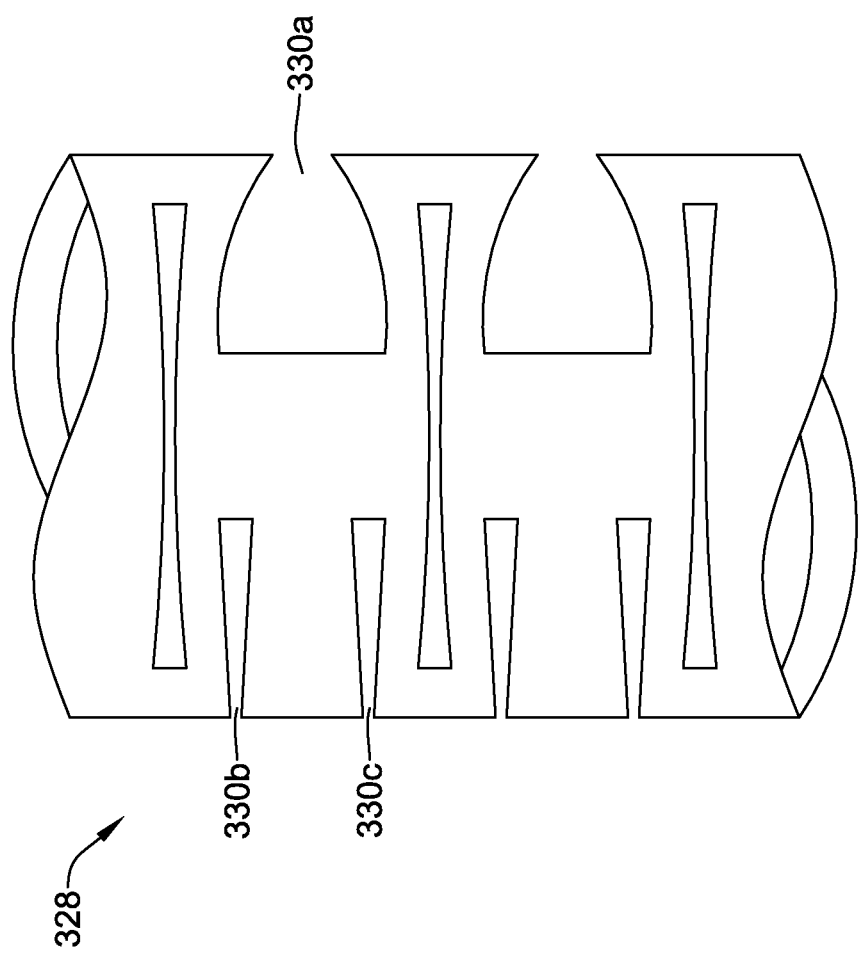
FIG. 8 is a perspective view of the tubular member illustrated in FIG. 7 under compression.

In some embodiments, the lateral flexibility characteristics of tubular member 328 may be altered. For example, tubular member 328 can be compressed into a compressed shape as illustrated in FIG. 8. Compression may be accomplished using any suitable method such as by threading tubular member 328 over a mandrel and then compressing tubular member 328 axially to the desired degree. In some embodiments, tubular member 328 can be compressed until at least some of narrow slots 330b/330c are completely closed. In other embodiments, some or all of slots 330b/330c may be only partially closed.

Once compressed, tubular member 328 can be set into the compressed shape using a suitable technique such as heat treating. In some embodiments, tubular member 328 includes a super-elastic and/or shape-memory material such as shape-memory nickel-titanium alloy so that heat treating may set tubular member 328 into the compressed shape. Variations on this general theme are contemplated for embodiments that utilize different materials.

The resulting structure may have wide slots 330a that are partially closed and narrow slots 330b/330c that are partially or completely closed. As such, bending tubular member 328 in one direction (e.g., toward wide slot 330a) might cause slots 330b/330c to open slightly. Because slots 330b/330c can open, this would define a preferential bending direction that is oriented toward wide slot 330a. Conversely, bending tubular member 328 in the opposite direction (e.g., toward narrow slots 330b/330c) may be more difficult as slots 330b/330c would be at or near a solid height (i.e., there are nearly or completely closed). Thus, tubular member 328 may have greater lateral stiffness in this direction and/or a "least" preferential bending direction. In addition to having a preferential bending direction, compressing tubular member 328 may additional provide tubular member 328 with a desirable level of compressive stiffness. This may be, for example, because slots 330b/330c, by virtue of being partially of completely closed, may tend to resist further compression.

Figure 9:
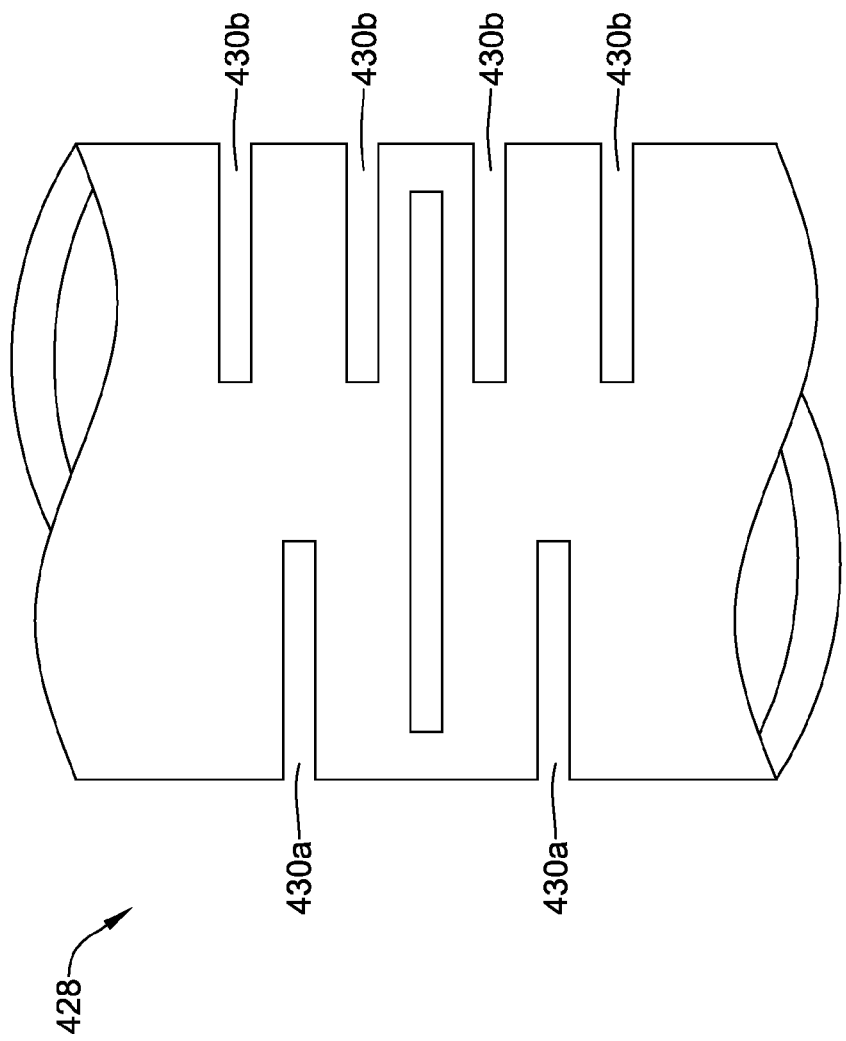
FIG. 9 is a perspective view of a portion of another example tubular member.

Another example tubular member 428 is illustrated in FIG. 9 that may be similar to other tubular members disclosed herein. Rather than utilizing wide and narrow slots like in tubular member 328, tubular member 428 includes slots that are distributed in different densities. For example, tubular member 428 may include a first set of slots 430a disposed on one side of tubular member 428 and a second set of slots 430b disposed on the opposite side of tubular member 428. Slots 430a and 430b may be distributed in different densities. For example, slots 430b may be arranged to have more slots per unit length than slots 430a. Because slots 430b are arranged in a higher density, tubular member 428 may have a preferential bending direction that is oriented toward slots 430b.

Figure 10:
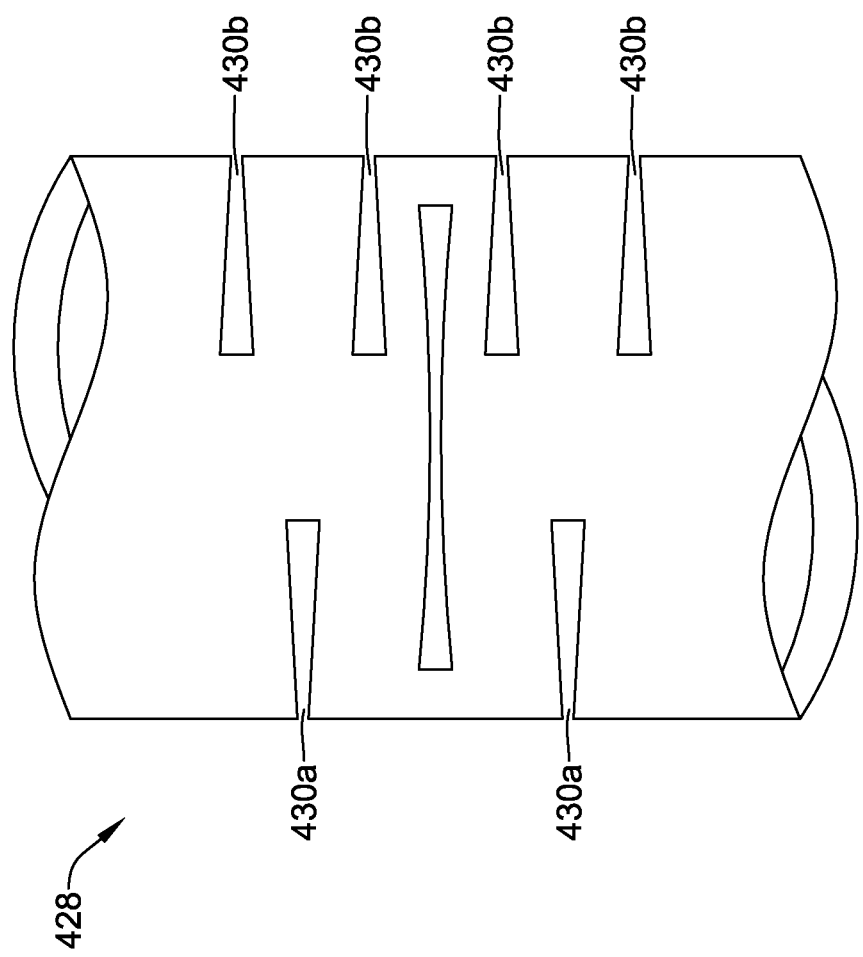
FIG. 10 is a perspective view of the tubular member illustrated in FIG. 9 under compression.

Placing tubular member 428 under compression, as illustrated in FIG. 10, may result in some of the same features as placing tubular member 328 under compression. For example, tubular member 428 may have a preferential bending direction that is oriented in the direction toward slots 430b. Likewise, the compressed version of tubular member 428 may have increased compressive stiffness.

Figure 11:
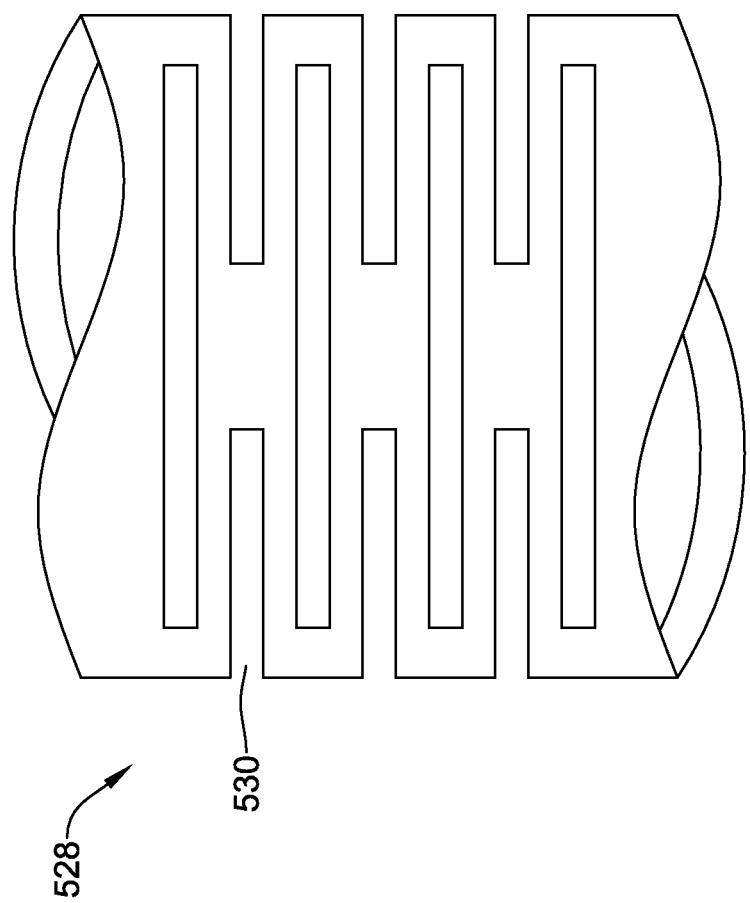
FIG. 11 is a perspective view of a portion of another example tubular member.
Figure 12:
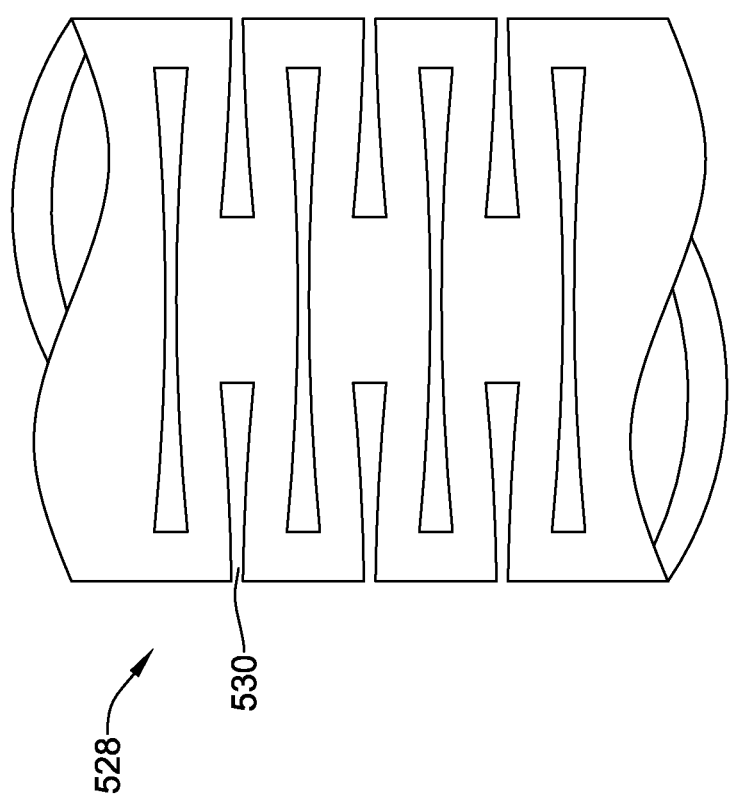
FIG. 12 is a perspective view of the tubular member illustrated in FIG. 11 under compression.

Another example tubular member 528 is illustrated in FIG. 11 that may be similar to other tubular members disclosed herein. Unlike tubular members 328/428, slots 530 in tubular member 528 may have the same width and be distributed in the same manner on both sides of tubular member 528 or in any suitable way including any of the patterns discussed below. Placing tubular member 528 under compression, as illustrated in FIG. 12, may provide tubular member 528 with a number of desirable features. For example, compressing tubular member 528 into a compressed shape and then setting tubular member 528 in the compressed shape may provide tubular member 528 with a desired level of compressive stiffness while maintaining a desired level of lateral flexibility. For example, when tubular member 528 (i.e., tubular member 528 as depicted in FIG. 12 in the compressed shape) is subjected to further compressive forces, slots 530, by virtue of being partially of completely closed, will tend to resist further compression. However, laterally flexing or bending tubular member 528 allows slots 530 to open and, thus, maintain a desired level of lateral flexibility.

With the above variations in arrangement, orientation, and configurations in mind, it can be appreciated that other variations are contemplated including variations in the materials that may be utilized for any portion of devices 10/110 and/or the various components thereof (including tubular members 28/128/228/328/428/528). It should be noted that any references to device 10/110 or a particular portion of either of devices 10/110 for variations in material composition or other variations may be applied to the various components of any of the devices 10/110 and/or components of devices (e.g., tubular members 28/128/228/328/428/528) disclosed herein.

In general, devices 10/110 and/or the various components thereof may include a variety of materials including metals, metal alloys, polymers (some examples of which are disclosed below), metal-polymer composites, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As alluded to above, within the family of commercially available nickel-titanium or nitinol alloys is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear or a somewhat but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2 to about 5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to about 0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about –60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point (e.g., there is no temperature at which the material experiences a dramatic shift in mechanical properties).

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol, can be used to achieve desired properties.

In at least some embodiments, portions or all of devices 10/110 and/or the various components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of devices 10/110 in determining their location. Some examples of radiopaque materials can include, but are not limited to, gold, platinum, palladium, tantalum, tungsten alloy, polymer material loaded with a radiopaque filler, and the like.

In some embodiments, a degree of MRI compatibility is imparted into devices 10/110 and/or the various components thereof. For example, to enhance compatibility with Magnetic Resonance Imaging (MRI) machines, it may be desirable to make portions or all of system 10 in a manner that would impart a degree of MRI compatibility. For example, portions or all of devices 10/110 may be made of a material that does not substantially distort the image and create substantial artifacts (artifacts are gaps in the image). Certain ferromagnetic materials, for example, may not be suitable because they may create artifacts in an MRI image. Portions or all of devices 10/110 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, different portions of devices 10/110 may be made from different materials. For example, a proximal section and distal section of tubular member 28 may be formed of different materials. In some embodiments, the material used to construct the proximal section can be formed of linear elastic nickel-titanium alloy and the distal section can be formed of a super-elastic nickel-titanium alloy. The proximal section and the distal section can be provided separately and joined together using a suitable connecting technique (e.g., welding such as including laser welding, soldering, brazing, swaging, adhesive, a mechanical bond or connection, crimping, or the like, or combinations thereof). Alternatively, tubular member 28 may begin as a single monolith of linear-elastic nickel-titanium alloy and then a portion (e.g., a distal portion) can be heat treated so as to impart the desired super-elastic properties.

Some examples of suitable polymers that may be utilized in the manufacturing of devices 10/110 and/or the various components thereof may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phosphate ester), poly(amino acid), polyacrylate, polyacrylamid, poly(hydroxyethyl methacrylate), polyurethane, polysiloxane and their copolymers, or mixtures or combinations thereof.

As indicated above, tubular members 28/128/228/328/428/528 may include a plurality of cuts, apertures, and/or slots 30/130/230a/230b/230c/230d//330a/330b/330c/430a/430b/530 formed therein. For simplicity purposes, the following discussion makes reference to only tubular member 28 and slots 30. This, however, is not intended to be limiting as any of the following slot-related features may be applied to any of the tubular members and/or slots disclosed herein, to the extent applicable, without departing from the spirit of the invention.

Slots 30 can be formed by methods such as micro-machining, saw-cutting (e.g., using a diamond grit embedded semiconductor dicing blade), laser cutting, electron discharge machining, grinding, milling, casting, molding, chemically etching or treating, or other known methods, and the like. In some such embodiments, the structure of the tubular member 28 is formed by cutting and/or removing portions of the tube to form slots 30. Some example embodiments of appropriate micromachining methods and other cutting methods, and structures for tubular members including slots and medical devices including tubular members are disclosed in U.S. Pat. Publication Nos. US 2003/0069522 and US 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing devices 10/110 may include forming slots 30 in tubular member 28 using any of these or other manufacturing steps.

Various embodiments of arrangements and configurations of slots 30 are contemplated. In some embodiments, at least some, if not all of slots 30 are disposed at the same or a similar angle with respect to the longitudinal axis of the tubular member 28. As shown, slots 30 can be disposed at an angle that is perpendicular, or substantially perpendicular, and/or can be characterized as being disposed in a plane that is normal to the longitudinal axis of tubular member 28. However, in other embodiments, slots 30 can be disposed at an angle that is not perpendicular, and/or can be characterized as being disposed in a plane that is not normal to the longitudinal axis of tubular member 28. Additionally, a group of one or more slots 30 may be disposed at different angles relative to another group of one or more slots 30. The distribution and/or configuration of slots 30 can also include, to the extent applicable, any of those disclosed in U.S. Pat. Publication No. US 2004/0181174, the entire disclosure of which is herein incorporated by reference.

Slots 30 may be provided to enhance the flexibility of tubular member 28 while still allowing for suitable torque transmission characteristics. Slots 30 may be formed such that one or more rings and/or turns interconnected by one or more segments and/or beams are formed in tubular member 28, and such rings and beams may include portions of tubular member 28 that remain after slots 30 are formed in the body of tubular member 28. Such an interconnected ring structure may act to maintain a relatively high degree of tortional stiffness, while maintaining a desired level of lateral flexibility. In some embodiments, some adjacent slots 30 can be formed such that they include portions that overlap with each other about the circumference of tubular member 28. In other embodiments, some adjacent slots 30 can be disposed such that they do not necessarily overlap with each other, but are disposed in a pattern that provides the desired degree of lateral flexibility.

Additionally, slots 30 can be arranged along the length of, or about the circumference of, tubular member 28 to achieve desired properties. For example, adjacent slots 30, or groups of slots 30, can be arranged in a symmetrical pattern, such as being disposed essentially equally on opposite sides about the circumference of tubular member 28, or can be rotated by an angle relative to each other about the axis of tubular member 28. Additionally, adjacent slots 30, or groups of slots 30, may be equally spaced along the length of tubular member 28, or can be arranged in an increasing or decreasing density pattern, or can be arranged in a non-symmetric or irregular pattern. Other characteristics, such as slot size, slot shape and/or slot angle with respect to the longitudinal axis of tubular member 28, can also be varied along the length of tubular member 28 in order to vary the flexibility or other properties. In other embodiments, moreover, it is contemplated that the portions of tubular member 28, such as a proximal section, a distal section, or the entire tubular member 28 may not include any such slots 30.

As suggested above, slots 30 may be formed in groups of two, three, four, five, or more slots 30, which may be located at substantially the same location along the axis of tubular member 28. Within the groups of slots 30, there may be included slots 30 that are equal in size (i.e., span the same circumferential distance around tubular member 28). In some of these as well as other embodiments, at least some slots 30 in a group are unequal in size (i.e., span a different circumferential distance around tubular member 28). Longitudinally adjacent groups of slots 30 may have the same or different configurations. For example, some embodiments of tubular member 28 include slots 30 that are equal in size in a first group and then unequally sized in an adjacent group. It can be appreciated that in groups that have two slots 30 that are equal in size, the beams (i.e., the portion of tubular member 28 remaining after slots 30 are formed therein) are aligned with the center of tubular member 28. Conversely, in groups that have two slots 30 that are unequal in size, the beams are offset from the center of tubular member 28. Some embodiments of tubular member 28 include only slots 30 that are aligned with the center of tubular member 28, only slots 30 that are offset from the center of tubular member 28, or slots 30 that are aligned with the center of tubular member 28 in a first group and offset from the center of tubular member 28 in another group. The amount of offset may vary depending on the depth (or length) of slots 30 and can include essentially any suitable distance.

It can be appreciated that changes in the slot depth in tubular member 228 may be utilized so as to make a tubular member have no preferential bending direction. For example, if slot 230*a* was cut deeper into tubular member 228, as well as other slots that may longitudinally align with slot 230*a*, tubular member 228 may have no preferred bending direction even though lumen 248 may be eccentrically arranged relative to the wall of tubular member 228. This is because deeper version of slot 230*a* (and its longitudinally-aligned counterparts) may increase the lateral flexibility of tubular member 228 toward slot 230*a*. This same feature may be utilized for other tubular members so as to make them have no preferred bending direction.

Other variations are contemplated for slots 30 including different geometries. For example, in some embodiments, slots 30 can be substantially "V-shaped", substantially "U-shaped", include one or more steps in width, be angled, be semicircular, have a rounded bottom, have a squared bottom, and the like, or include combinations and/or variations thereof. Such geometries may be achieve through the used of a correspondingly shaped cutting member, through the use of a suitable cutting technique, or in any other suitable manner.

Numerous other arrangements are contemplated that take advantage of the various arrangements and/or configurations discussed above.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate core member having a proximal portion and a distal portion;
   a tubular member disposed about the distal portion, the tubular member having a plurality of slots formed therein;
   wherein the tubular member has a proximal end, a distal end, a longitudinal axis extending therebetween, and a plane extending through the longitudinal axis and along the length of the longitudinal axis, where the plane defines a first side of tubular member and a second side of the tubular member; and
   wherein a wide slot is disposed along the first side of the tubular member, and wherein a plurality of narrow slots are disposed directly opposite the wide slot along the second side of the tubular member opposite the first side, the wide slot being longer in the longitudinal direction than each of the plurality of narrow slots.

2. The medical device of claim 1, wherein the tubular member includes a nickel-titanium alloy.

3. The medical device of claim 2, wherein the tubular member includes a linear-elastic nickel-titanium alloy.

4. The medical device of claim 2, wherein a first portion of the tubular member includes a linear-elastic nickel-titanium alloy and a second portion of the tubular member includes a super-elastic nickel-titanium alloy.

5. The medical device of claim 4, wherein the first portion is a proximal portion of the tubular member.

6. The medical device of claim 1, wherein the tubular member has a first bending stiffness along the first side, wherein the tubular member has a second bending stiffness along the second side, and wherein the first bending stiffness is lower than the second bending stiffness.

7. The medical device of claim 6, further comprising a tension member disposed within the tubular member.

8. The medical device of claim 7, wherein tension forces can be selectively changed in the tension member.

9. The medical device of claim 7, wherein the tension member is under tension and wherein the tubular member includes a curved region that curves along the first side.

10. The medical device of claim 1, wherein the wide slot has a first width, wherein the plurality of narrow slots each have a second width, and wherein the first width is at least twice as long as the second width.

11. The medical device of claim 1, wherein the tubular member is manufactured by applying compression to the tubular member to define a compressed shape and heat treating the tubular member to set the tubular member in the compressed shape.

12. The medical device of claim 11, wherein the wide slot is only partially closed when the tubular member is in the compressed shape and wherein at least some of the narrow slots are closed when the tubular member is in the compressed shape.

* * * * *